United States Patent
Kasch et al.

[11] Patent Number: 5,162,312
[45] Date of Patent: Nov. 10, 1992

[54] 11β-SUBSTITUTED 16α, 17α-METHYLENE-ESTRA-4,9-DIEN-3-ONES

[75] Inventors: Helmut Kasch; Reimar Krieg; Anatoil Kurischko; Kurt Ponsold, all of Jena, Fed. Rep. of Germany

[73] Assignee: Schering Aktiengesellschaft, Berlin and Bergkamen, Fed. Rep. of Germany

[21] Appl. No.: 567,375

[22] Filed: Aug. 15, 1990

[51] Int. Cl.⁵ ............... A61K 31/07; A61K 31/56; C07J 3/00
[52] U.S. Cl. .................... 514/179; 514/182; 552/514; 552/519; 552/520; 552/526; 552/603
[58] Field of Search ........... 552/514, 519, 520, 526, 552/603; 514/179, 182

[56] References Cited

U.S. PATENT DOCUMENTS 4,450,107 5/1984 Nickisch et al. ............... 514/182

OTHER PUBLICATIONS

Loozen et al; Chemical Abstract 109(19), 1988 109(15), 1988, #170799d & 120463b.

Primary Examiner—Mukund J. Shah
Assistant Examiner—Y. N. Gupta
Attorney, Agent, or Firm—Millen, White & Zelano

[57] ABSTRACT

11β-substituted-16α, 17α-methylene-estra-4,9-dien-3-ones of formula I

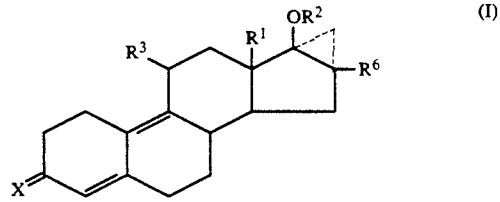

wherein
$R^1$ is a methyl or ethyl group;
$R^2$ is H; a $C_{1-6}$-alkyl, -alkoxymethyl, -alkanoyl or -alkoxcarbonyl group; 2-methoxyethyl; 2-hydroxyethyl; 2-$C_{1-4}$-alkanoyloxyethyl; or a tri-$C_{1-4}$-alkylsilyl group;
$R^3$ is vinyl; a $C_{1-6}$-alkyl; or a phenyl radical para-substituted by —OCH$_3$, —SCH$_3$, —N(CH$_3$), —CN, —CHO, CH$_3$CO—, CH$_3$CHOH— or —CH$_2$OH;
$R^6$ is H or a $C_{1-4}$-alkyl group;
X is O, a hydroxy- or methoxyimino group (=N~OH or —N~OCH$_3$), or a cyclic thioketal with 2 or 3 carbon ring atoms are provided, as well as pharmaceutical compositions containing said compounds, methods of use of said compounds, and processes for their production.

10 Claims, No Drawings

11β-SUBSTITUTED 16α,17α-METHYLENE-ESTRA-4,9-DIEN-3-ONES

This invention relates to 11beta-substituted 16alpha,17alpha-methylene-estra-4,9-dien-3-ones of the general formula I

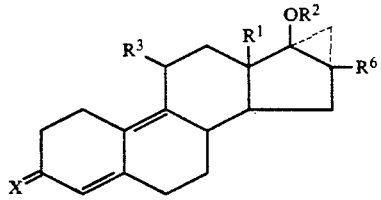

in which
R$^1$ means a methyl or ethyl group,
R$^2$ means a hydrogen, an alkyl, alkoxymethyl, alkanoyl, alkoxycarbonyl group, each with a carbon chain of 1 to 6 carbon atoms, 2-methoxyethyl, 2-hydroxyethyl, 2-alkanoyloxyethyl, (alkanoyl-C$_1$-C$_4$) or a trialkylsilyl group with alkyl radicals of 1 to 4 carbon atoms,
R$^3$ means a vinyl, C$_1$ to C$_6$ alkyl or a para-substituted phenyl radical with —OCH$_3$, —SCH$_3$, —N(CH$_3$)$_2$, —NHCH$_3$, —CN, —CHO, CH$_3$CO, CH$_3$CHOH or CH$_2$OH as para-substituent,
R$^6$ means a hydrogen atom or an alkyl group with 1 to 4 carbon atoms and
X means an oxygen atom, a hydroxy or methoxyimino grouping N OH or N OCH$_3$ or a cyclic thioketal with 2 or 3 carbon ring atoms.
Preferably in this case
R$^1$ means a methyl group,
R$^2$ means a hydrogen atom, a C$_1$ to C$_6$ alkyl group, a trialkylsilyl group with alkyl radicals with 1 to 4 carbon atoms, an acetyl, —CH$_2$OCH$_3$— or 2-methoxyethyl group,
R$^3$ means a vinyl radical or para-substituted phenyl radical with N(CH$_3$)$_2$, —CHO, —C(O)CH$_3$, —OCH$_3$ as a para-substituent,
R6 means a hydrogen atom or a methyl group and
X means an oxygen atom.

The compounds according to the invention which are especially preferred are
-17beta-ethoxy-11beta-(4-methoxyphenyl)-16alpha,17alpha-methylene-estra-4,9-dien-3-one,
-11beta-(4-dimethylaminophenyl)-17beta-methoxy-16alpha,17alpha-methylene-estra-4,9-dien-3-one,
-11beta-(4-dimethylaminophenyl)-17beta-ethoxy-16alpha,17alpha-methylene-estra-4,9-dien-3-one,
-17beta-butyloxy-11beta-(4-dimethylaminophenyl)-16alpha,17alpha-methylene-estra-4,9-dien-3-one,
-11beta-(4-acetylphenyl)-17beta-methoxy-16alpha,17alpha-methylene-estra-4,9-dien-3-one,
-11beta-(4-acetylphenyl)-17beta-ethoxy-16alpha,17alpha-methylene-estra-4,9-dien-3-one,
-11beta-(4-acetylphenyl)-17beta-butyloxy-16alpha,17alpha-methylene-estra-4,9-dien-3-one,
-11beta-(4-acetylphenyl)-17beta-hexyloxy-16alpha,17alpha-methylene-estra-4,9-dien-3-one,
-11beta-(4-acetylphenyl)-17beta-methoxyethyloxy-16alpha,17alpha-methylene-estra-4,9-dien-3-one,
-11beta-(4-formylphenyl)-17beta-methoxy-16alpha,17alpha-methylene-estra-4,9-dien-3-one and
-17beta-ethoxy-11beta-(4-formylphenyl)-16alpha,17alpha-methylene-estra-4,9-dien-3-one,
-17beta-(dimethyl-tert-butylsiloxy)-11beta-(4-methoxyphenyl)-16alpha,17alpha-methylene-estra-4,9-dien-3-one,
-11beta-(4-dimethylaminophenyl)-17beta-(dimethyl-tert-butylsiloxy)-16alpha,17alpha-methylene-estra-4,9-dien-3-one,
-11beta-(4-acetylphenyl)-17beta-(dimethyl-tert-butylsiloxy)-16alpha,17alpha-methylene-estra-4,9-dien-3-one,
-17beta-hydroxy-11beta-(4-methoxyphenyl)-16alpha,17alpha-methylene-estra-4,9-dien-3-one,
-11beta-(4-dimethylaminophenyl)-17beta-hydroxy-16alpha,17alpha-methylene-estra-4,9-dien-3-one,
-11beta-(4-acetylphenyl)-17beta-hydroxy-16alpha,17alpha-methylene-estra-4,9-dien-3-one,
-17beta-acetoxy-11beta-(4-dimethylaminophenyl)-16alpha,17alpha-methylene-estra-4,9-dien-3-one,
-17beta-acetoxy-11beta-(4-acetylphenyl)-16alpha,17alpha-methylene-estra-4,9-dien-3-one,
-11beta-(4-dimethylaminophenyl)-17beta-methoxymethyl-16alpha,17alpha-methylene-estra-4,9-dien-3-one,
-11beta-(4-acetylphenyl)-17beta-methoxymethyl-16alpha,17alpha-methylene-estra-4,9-dien-3-one,
-11beta-(4-dimethylaminophenyl)-17beta-methoxy-16beta-methyl-16alpha,17alpha-methylene-estra-4,9-dien-3-one and
-11beta-(4-acetylphenyl)-17beta-methoxy-16alpha,17alpha-methylene-estra-4,9-dien-3-one.

The compounds of the general formula I have a strong affinity for the gestagen receptor, without themselves developing gestagen activity. They are competitive antogonists of progesterone (antigestagen); since they displace from the receptor the progesterone necessary for maintenance of pregnancy, they are suitable for triggering abortions and for inducing labor.

Besides said indications, the compounds according to the invention can also be used for treatment of endometriosis, dysmenorrhea and endocrine hormone-dependent tumors such as, e.g., breast cancer and meningioma.

The abortive action of the substances, determined by animal experiments, serves for characterizing the antigestagen action. For this purpose, female pregnant rats (positive sperm detection—1st day of pregnancy) weighing between 180 and 200 g were treated subcutaneously with the test compound, suspended in peanut oil, on the 5th to 8th day of pregnancy. After autopsy on the 20th day of pregnancy, the uteri were examined. In this case, the number of pregnant females and the average number of fetuses per pregnant animal were determined. The inhibitory effect was calculated as follows:

$$He = \left(1 - \frac{x_v \cdot n_k}{m_v \cdot x_k}\right) \cdot 100 \, (\%)$$

x=number of pregnant females
n=number of impregnated females v=test group
k=control group

| Group Substance | Total Dosage (mg/animal/4d) | N | Fertility Inhibition abso. | rel. % |
|---|---|---|---|---|
| 17beta-methoxy-11beta-(acetylphenyl) | 3 | 6 | 6 | 100 |

| Group Substance | Total Dosage (mg/animal/4d) | N | Fertility Inhibition abso. | rel. % |
|---|---|---|---|---|
| 17beta-methoxy 11beta-(dimethylamino-phenyl) | 3 | 6 | 6 | 100 |
| 17beta-ethoxy-11beta-(acetylphenyl) | 3 | 6 | 6 | 100 |
| 17beta-ethoxy-11beta-(dimethylaminophenyl) | 3 | 6 | 4 | 67 |
| 17beta-(methoxyethyl-11beta-(acetylphenyl) | 3 | 6 | 6 | 100 |
| Control | | 6 | 0 | 0 |
| Comparison (RU 48G[1]) | 3 | 6 | 6 | 100 |

The compounds according to the invention of general formula I can be used in the form of pharmaceutical preparations. The production of preparations takes place according to methods galenical medicine known in the art by mixing with an organic or inorganic inert vehicle which is suitable for enteral, percutaneous or parenteral administration.

The dosage of the compounds according to the invention for the indicated indications is between 1 and 1000 mg daily.

The compounds of general formula I are produced according to the invention by a compound of the general formula XI

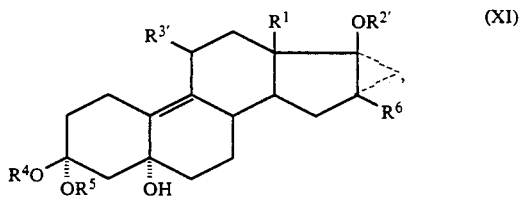

in which
$R^1$ means a hydrogen atom or a methyl group and
$R^4$ and $R^5$ each mean a methyl or ethyl group or together an ethylene group or 2,2-dialkylpropylene group, especially 2,2-dimethylpropylene group, and
$R^{2'}$ and $R^{3'}$ have the same meaning as $R^2$ and $R^3$ in formula 1, and optionally present keto groups are protected, the latter being converted by acid treatment in a water-miscible solvent to 11beta-substituted 16alpha,1-7alpha-methylene-estra-4,9-dien-3-one of general formula I and these then optionally being derivatized by oximation, thioketalization or acylation to another compound of general formula I.

As acids for the acid treatment, there are used, e.g., aqueous acetic acid, p-toluenesulfonic acid or mineral acids such as hydrochloric acid, sulfuric acid, phosphoric acid or perchloric acid, and as solvents, there is used aqueous methanol, ethanol, or acetone. It is optionally heated during the acid treatment to 60° C. to 70° C.

The further derivatization takes place by oximation or thioketalization in 3-position and with the presence of a 17betahydroxy group optionally by its acylation, and other compounds according to the invention of general formula I are formed.

The 17beta-hydroxy compounds necessary for this purpose are produced optionally by saponification of the corresponding silylalkyl ethers with pyridinium tosylate in methanol.

The thioketalization is performed with ethanedithiol or propanedithiol in the presence of a Lewis acid such as boron trifluoride etherate.

The oximation takes place with hydroxylamine hydrochloride or methoxyamine hydrochloride in an alcoholic solution in the presence of a base such as $Na_2CO_3$, $K_2CO_3$, dilute NaOH or KOH.

The acylation of the 17beta-OH group takes place with the corresponding acid anhydride or chloride in the presence of catalytic amounts of a pyridine base, such as pyridine itself or 4-(dimethylamino)-pyridine.

The production of the initial products of general formula XI to be used according to the invention takes place according to the diagram below:

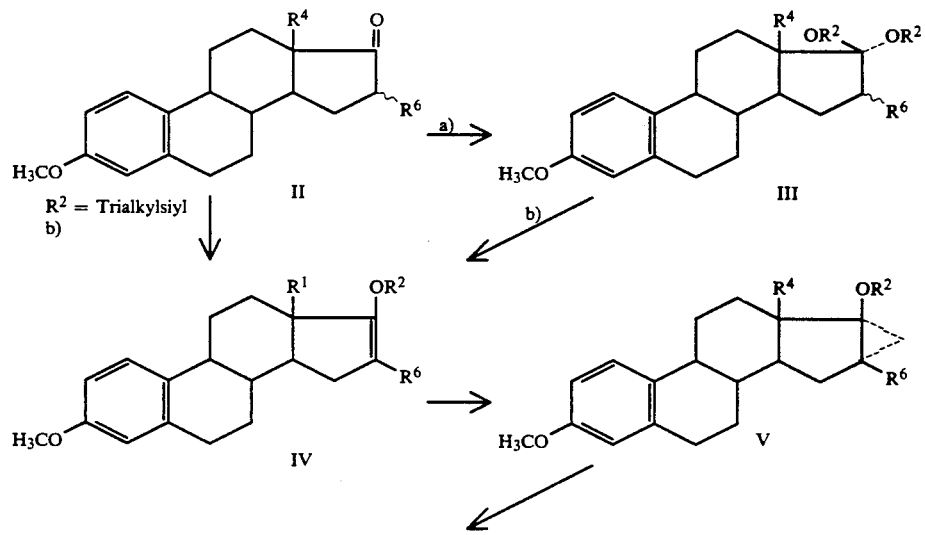

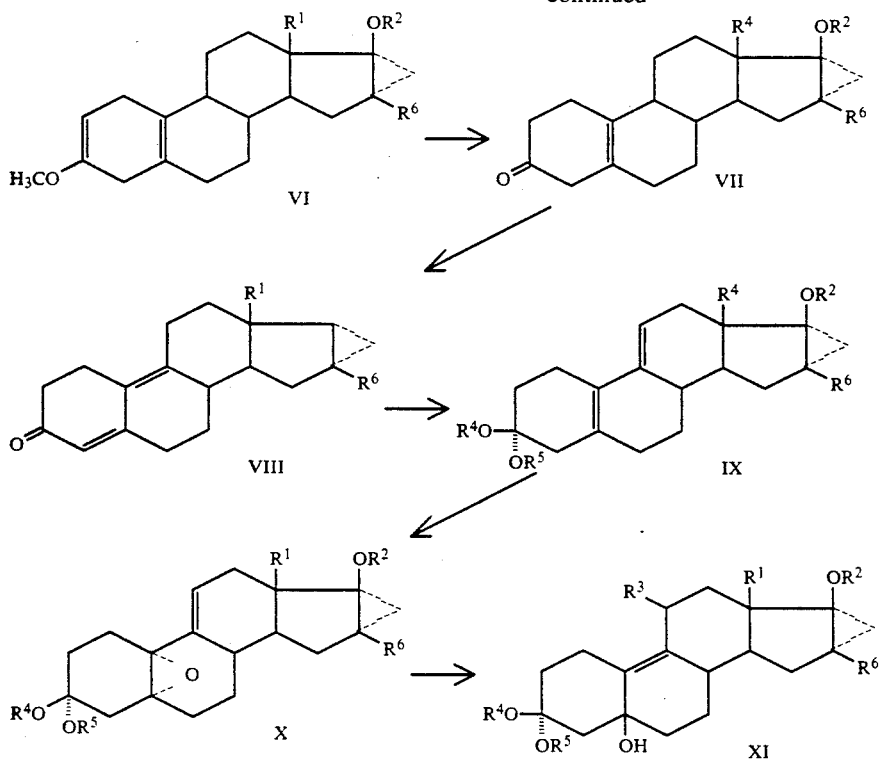

Depending on the 17-substituents desired, either a) 3-methoxy-gona-1,3,5(10)-trien-17-ones of general formula II are converted by an alcohol in the presence of catalytic amounts of an acid to the 17-ketals of general formula III, b) these ketals are reacted by thermolysis at 120° C. to 180° C. to the 17-alkylenol ethers of general formula IV, or b') 3-methoxy-gona-1,3,5(10)-trien-17-ones of general formula II are converted with trialkylsilyl halides or -trifluoromethanesulfonates in the presence of a base directly to the silylenol ethers of general formula IV, in which $R_2$ stands for trialkylsilyl, c) 17-enol ethers IV according to Simmons-Smith is converted to the 16alpha,17alpha-methylene compounds of general formula V, d) 16alpha,17alpha-methylene compounds V are reduced by Birch reduction to the 3-enol ethers of general formula VI, e) the 3-keto-5(10) compounds of general formula VII are produced from 3-enol ethers VI by catalytic amounts of acid in an aqueous organic solvent, f) 3-keto-5(10) compounds VII are reacted by bromation-dehydrobromation to the 16alpha,17alpha-methylene-estra-4,9-dien-3-ones of general formula VIII, g) 16alpha,17alpha-methylene-estra-4,9-dien-3-ones VIII are converted by ketalization with an alcohol in the presence of catalytic amounts of an acid to the ketals of general formula IX, in which $R_4=R_5$—$CH_3$, $C_2H_5$ or a cyclic ketal with 2 or 3 C ring atoms, h) the 5alpha,10alpha-epoxides of general formula X are produced by epoxidation from these ketals IX, and i) the 5alpha,10alpha-epoxides X are arylated with arylmagnesium halide in the presence of a Cu(I) salt at a reaction temperature of −30° C. to +30° C. to the 11beta-aryl16alpha,17alpha-methylene compounds of general formula XI.

In process step a), there are preferably used as alcohols, methanol, ethanol, propanol, butanol, pentanol, hexanol, ethylene glycol monomethyl ether and acetic acid monoglycol ester; as acids, sulfuric acid and p-toluenesulfonic acid; and the reaction is performed in the presence of dehydrating agents, such as formic acid trimethyl ester and formic acid triethyl ester, as well as optionally by adding a solvent, such as methylene chloride, chloroform, benzene, toluene, xylene or mesitylene. In process step b) the thermolysis is optionally performed with addition of acid, such as p-toluenesulfonic acid, sulfuric acid or $KHSO_4$ as well as a high-boiling entraining agent such as xylene or mysitylene; in this way the solvent optionally is removed continuously under reduced pressure.

If variant b') is selected for the first two reaction steps, i.e. if $R^2$ is to be a trialkylsilyl radical in the compound of general formula IV, preferably as tiralkylsilyl halide trimethylsilyl or dimethyl-tert-butylsilyl in the form of chlorides, bromides or iodides are used, and the reactive trialkylsilyl iodides are produced in situ from the trialkylsilyl chlorides and NaI, trimethyl- and diemthyl-tert-butylsilyltriflate are used as trialkylsilyl trifluoromethanesulfonates, lithium diisopropylamide or amines such as triethylamine, pyridine and imidazole are used as bases and work is done in an aprotic solvent, such as diethyl ether, tetrahydrofuran, dioxane, N,N-dimethylformamide, acetonitrile or n-methylpyrrolidone.

In process step c), the Simmons-Smith reaction is performed with methylene bromide or iodide in the presence of Zn or Zn transition metal pairs, such as Zn/Cu, Zn/Ag or Zn/Co pairs, with addition of an ether, such as diethyl ether, diisopropyl ether, or dimethoxyethane, and optionally a solubilizer such as benzene, toluene or methylene chloride.

In process step d), for the Birch reduction, there are used alkali or alkaline-earth metals, such as lithium, sodium, potassium or calcium, in liquid ammonia with addition of an alcohol, such as ethanol, n-propanol, isopropanol or tert-butanol, and optionally a solubilizer, such as dioxane or tetrahydrofuran.

In process step e), for the enol ether cleavage, as acids, there are used acetic acid, oxalic acid, pyridinium tosylate, p-toluenesulfonic acid and dilute sulfuric acid, as aqueous organic solvents, there are used aqueous acetone, aqueous methanol or a homogeneous solvent mixture consisting of water, methylene chloride and tert-butanol.

In process step f), the bromation/dehydrobromation is performed by pyridine hydrobromide perbromide or bromine in pyridine.

In process step g), the ketalization of the 3-keto group is performed in the presence of a dehydrating agent, such as formic acid trimethyl ester or formic acid triethyl ester, or in the presence of a water entrainer, such as chloroform, benzene or toluene, and as alcohols, there are used methanol, ethanol, ethylene glycol or 2,3-dimethylpropanediol and as acids, there are used p-toluenesulfonic acid, oxalic acid or pyridinium tosylate. The 17-alcohol function must be protected before the ketalization in the form of an ester or dimethyl-tert-butylsilyl ether.

In process step h), the epoxidation is performed with $H_2O_2$ and chloral hydrate in the presence of a buffer as well as of $Na_2HPO_4$, $NaH_2PO_4$, $Na_2CO_3$, $NaHCO_3$, $K_2CO_3$ or of $KHCO_3$ in the form of the anhydrous salts in methylene chloride or chloroform.

In process step i), the Grignardization is performed in an ether, such as diethyl ether, tetrahydrofuran or dioxane, optionally with addition of a solubilizer, such as benzene or toluene, further, as aryl magnesium halides, there are used phenylmagnesium halides, which in p-position to magnesium contain an $OCH_3$-, $SCH_3$-, $N(CH_3)_2$, $NHCH_3$-, CN-, $CH_3CHOH$-, $CH(OR_3)(OR_4)$- or $CH_3C-(OR_3)(OR_4)$ group and in which halide means bromide or chloride, and as Cu(I) salts, there are used CuCN, CuI and CuCl.

The following embodiments provide for a more detailed explanation of the invention.

EXAMPLE 1 a) 3,17,17-trimethoxy-estra-1,3,5(10)-triene 5 g of 3-methoxy-estra-1,3,5(10)-trien-17-one (17.5 mmol), 15 ml of absolute methanol, 0.35 g of p-toluenesulfonic acid and 6 ml of formic acid trimethyl ester are stirred in a 100-ml three-necked flask with exclusion of water at 50° C. for about 2.5 hours. After the reaction has been completed, the reaction mixture is used directly in the next step or is mixed with triethylamine and hexane, after cooling, for completion of the precipitation. After repeated recrystallization from heptane, 5.45 g (94% of theory) is obtained, melting point: 104° C. to 116° C.

b) 3,17-dimethoxy-estra-1,3,5(10),16-tetraene

The reaction solution containing the 3,17,17-trimethoxy-estra-1,3,5(10)-triene is heated under inert gas for 30–40 minutes to 140° C. to 160° C., and the solvent is gradually distilled off. Finally, it is heated at this temperature for 2 hours in a vacuum and the resulting enol ether is used in the next step in the form of the crude product without purification, melting point: 90.5° C. to 93° C.

$IR[cm^{-1}]$: 1610, 1565, 1490 (aromatic), 1610 (enol superimposed).

c) 3,17-dimethoxy-16alpha,17alpha-methylene-estra-1,3,5(10)-triene 10 g of 3,17-dimethoxy-estra-1,3,5(10),16-tetraene is dissolved in 50 ml of toluene and 40 ml of dimethoxyethane and, after addition of 20 g of Zn/Cu catalyst first under gentle heating, is gradually mixed with 15 ml of methylene iodide with vigorous stirring in an inert gas atmosphere. The addition of methylene iodide in this case is to be performed so that the reaction temperature does not exceed 50° C. After quieting down of the exothermal reaction, it is stirred for 4 hours at 50° C. and then filtered from the catalyst. The filtrate is mixed with an aqueous ammonium chloride solution and the steroid is extracted with toluene. The residue remaining after the concentration of the toluene extracts by evaporation is flash chromatographed on basic aluminum oxide with a benzene/n-hexane mixture (1:1). The crude product obtainable after the concentration by evaporation is crystallized from hexane. 6.5 g of the 16alpha,17alpha-methylene compound is obtained, melting point: 128° C. to 130° C., $[\alpha]_D = 93.5°$.

d) 3,17-dimethoxy-16alpha,17alpha-methylene-estra-2,5(10)diene 10 g of sodium, which is cut into small cubes, is carefully added to a solution of 175 ml of tetrahydrofuran and 500 ml of liquid ammonia under protective gas at −50° C. After the dissolution of the sodium, 70 ml of tert-butanol is added and then 75 ml of tetrahydrofuran solution containing 10 g of 3,17-dimethoxy-16alpha,17alpha-methylene-estra-1,3,5(10)-triene is slowly instilled. Then it is stirred for 4 hours at about −33° C. and then mixed with about 10 ml of methanol, and the optionally still blue solution is bleached. The ammonia is allowed to evaporate and the steroid is precipitated with water. After fritting and drying, 10 g of the 16alpha,17alpha-methylene enol ether is obtained, which can be crystallized from methanol, melting point: 136° C. to 139° C.

$IR[cm^{-1}]$: 1670 and 1695 (enol ether).

e) 17beta-methoxy-16alpha,17alpha-methylene-estr-5(10)-en-3-one 10 g of 3,17-dimethoxy-16alpha,17alpha-methylene-estra-2,5(10)-diene is suspended in 165 ml of 80% aqueous acetone and is mixed with vigorous stirring with 0.2 ml of 25% sulfuric acid. Then, with stirring, it is heated on the water bath (60° C.) until all the steroid has gone into solution (about 30 minutes). Then, it is allowed to cool to room temperature and stirred one more hour. After the reaction has been completed, the steroid is precipitated by the addition of water, separated and dried. 9.5 g of crystalline 16alpha,17alpha-methylene compound, which was used in the next step without recrystallization, is obtained.

$IR[cm^{-1}]$: 1705 (3-ketone).

f)
17beta-methoxy-16alpha,17alpha-methylene-estra-4,9-dien-3-one 9.5 g of 17beta-methoxy-16alpha,17alpha-methylene-estr-5(10)-en-3-one (crude product) is dissolved in 130 ml of pyridine and then, with cooling ($-5°$ C.), mixed with 11.5 of pyridine hydrobromide perbromide within 5 minutes. Then, the cooling is removed and the reaction solution warming slowly to room temperature is stirred for about 30 minutes, and then mixed with 3 ml of methylbutene and an excess bromation agent is consumed. Then, it is stirred for 4 hours at room temperature and then stirred into ice water, and the steroid precipitates in oily crystalline form. For complete crystallization, it is stored for 16 hours in the refrigerator and the steroid is fritted. 8 g of crystalline crude product is obtained. After extraction with methylene chloride and chromatography on neutral aluminum oxide with benzene/ethyl acetate (20:1 to 9:1), about 1 g of dienone can be obtained from the filtrate, dienone which can be crystallized from acetone/n-hexane (total yield 9 g). Melting point: 117° C. to 121° C., $[\alpha]_D = -203°$.

g)
3,3-ethylenedioxy-17beta-methoxy-16alpha,17alpha-methylene-estra-5(10),9(11)-diene 8 g of 17beta-methoxy-16alpha,17alpha-methylene-estra-4,9-dien-3-one (crystalline crude product) is dissolved in 100 ml of benzene, mixed with 6.8 ml of glycol and 0.2 g of p-toluenesulfonic acid and boiled on the water separator with vigorous stirring for 2 hours. Then, the cooled solution is stirred in a saturated sodium bicarbonate solution and the steroid is extracted with benzene. The residue obtainable after concentration by evaporation is crystallized from ether/n-hexane, and 7 g of ketal is obtained, melting point: 79° C. to 84° C., $[\alpha]_D = 220.6°$.

h)
3,3-ethylenedioxy-17beta-methoxy-alpha,17alpha-methylene-5alpha,10alpha-oxido-estr-9(11)-ene 9 g (crude product) of 3,3-ethylenedioxy-17beta-methoxy-16alpha,17alpha-methylene-estra-5(10),9(11)-diene, 2 g of anhydrous Na$_2$HPO$_4$ and 1 g of Na$_2$CO$_3$ are suspended in 45 ml of methylene chloride and mixed with stirring at room temperature with 7.25 ml of 30% H$_2$O$_2$ and finally, mixed with 1.25 ml of chloral hydrate. Then, it is stirred for 20 hours at room temperature and following that, an aqueous sodium carbonate solution is added and the steroid is extracted with methylene chloride. The organic phase is washed twice more with a sodium carbonate solution and finally with water, then is dried and concentrated by evaporation. The oily residue is chromatographed on basic Al$_2$O$_3$ with benzene/ethyl acetate (20:1 to 9:1). 6.6 g of 5alpha,10alpha epoxide is obtained in the form of an oil.

i)
11beta-(4-dimethylaminophenyl)-3,3-ethylenedioxy-17beta-methoxy-16alpha,17alpha-methylene-estr-9-en-5alpha-ol 30 ml of a Grignard solution, prepared from 0.96 g of magnesium, 5 ml of tetrahydrofuran, 0.05 ml of dibromoethane and 8.4 g of p-bromodimethylaminobenzene in 55 ml of tetrahydrofuran, is cooled to about $-15°$ C. and mixed with 0.25 g of CuCl. After 15 minutes, about 2.34 g of 3,3-ethylenedioxy-17beta-methoxy-16alpha,17alpha-methylene-5alpha,10alpha-oxido-estr-9(11)-ene, which is dissolved in 10 ml of tetrahydrofuran, is instilled cold. Then, it is allowed to warm slowly to room temperature. After one hour, all the initial material is reacted. It is mixed with aqueous ammonium chloride solution and the steroid is extracted with ether. The organic phase is washed with water, then dried and concentrated by evaporation. After chromatography on basic aluminum oxide, the elution takes place with benzene/ethyl acetate (20:1 to 9:1), 2.29 g of the 11beta dimethyl-aminophenyl compound is obtained, which can be crystallized from methanol, melting point 151° C. to 156° C., $[\alpha]_D = 43.6°$.

j)
11beta-(4-dimethylaminophenyl)-17beta-methoxy-16alpha,17alpha-methylene-estra-4,9-dien-3-one 0.4 g of 11beta-(4-dimethylaminophenyl)-3,3-ethylenedioxy-17beta-methoxy-16alpha,17alpha-methylene-estr-9-en-5alpha-ol is dissolved in 7 ml of 70% aqueous acetic acid and heated for 1 hour at a 60° C. water bath temperature with stirring. After the reaction has been completed, it is stirred in cold water, which contains some ammonia for neutralization of the acid. The precipitated product is separated and flash chromatographed on neutral aluminum oxide with a benzene/ethyl acetate mixture (10:1). After crystallization from methanol/water, 0.3 g of the dimethylaminophenyl compound is obtained, melting point: 87° C. to 91° C., $[\alpha]_D = 295.2°$.

EXAMPLE 2

The production of reaction steps a to h takes place analogously to example 1.

a)
3,3-ethylenedioxy-17beta-methoxy-16alpha,17alpha-methylene-11beta-[4-(2'-methyl-1',3'-dioxolan-2'-yl)phenyl]estr-9-en-5alpha-ol 0.05 ml of dibromoethane is added to a suspension of 0.72 g of magnesium chips in 5 ml of tetrahydrofuran and mixed gradually under argon with 55 ml of a tetrahydrofuran solution containing 7.35 g of p-bromo-(2'-methyl-1',3'-dioxolan-2'-yl)-benzene, so that the inner temperature does not exceed 45° C. In the starting phase, it is slightly heated (45° C.) and after the Grignard has started, the temperature is regulated by the addition of the aryl halide. After the addition is completed, it is stirred for 2 more hours at 45° C. 37 ml is removed from the thus prepared Grignard solution and is mixed with 0.15 g of CuCl with cooling ($-5°$ C. to $-15°$ C.). It is stirred for 15 minutes while maintaining this temperature and then a solution of 2 g of 3,3-ethylenedioxy-17beta-methoxy-16alpha,17alpha-methylene-5alpha,10alpha-oxido-estr-9(11)-ene (1 h) in 10 ml of tetrahydrofuran is added cold so that the solution is not substantially warmed. After the reaction has been completed, it is mixed with an aqueous ammonium chloride solution and the steroid is extracted with ether. After the concentration by evaporation, the remaining residue is chromatographed on basic aluminum oxide with benzene/ethyl acetate (20:1 to 9:1). 1.5 g of the 11beta-aryl compound, which can be crystallized from ether/n-hexane, is obtained, melting point: 137° C. to 144° C., $[\alpha]_D = 31.2°$.

j)
11beta-(4-acetylphenyl)-17beta-methoxy-16alpha,17alpha-methylene-estra-4,9-dien-3-one 0.45 g of 3,3-ethylenedioxy-17beta-methoxy-16alpha,17alpha-methylene-11beta-[4-(2'-methyl-1',3'-dioxolan-2'-yl)-phenyl]estr-9-en-5alpha-ol is dissolved in 10 ml of 70% aqueous acetic acid and stirred on the water bath at 60° C. for about 1 hour. After the reaction has been completed, the solution is mixed cold with water, and 0.3 g of the steroid is precipitated in amorphous crystalline form. After chromatography on basic aluminum oxide with benzene/ethyl acetate (20:1), 0.2 g of 4,9-diene, which is crystallized from methanol/water, is obtained, melting point: 84° C. to 87° C., $[\alpha]_D=279.2°$.

EXAMPLE 3

The production of reaction steps a to h takes place analogously to example 1.

i)
11beta-[4-(diethoxymethyl)-phenyl]-3,3-ethylenedioxy-17-methoxy-16alpha,17alpha-methylene-estr-9-en-5alpha-ol 30 ml (15 mmol) of a p-diethoxymethylphenyl magnesium bromide solution in tetrahydrofuran, prepared from 0.72 g of magnesium chips, 7 ml (8.85 g, 30 mmol) of p-bromodiethoxymethylbenzene in 60 ml of tetrahydrofuran and 0.05 ml of dibromoethene at a maximum temperature of 45° C., is cooled by dry ice to about −15° C. and mixed with 0.2 g of CuCl. After a 15-minute stirring, 1 g (oil; 2.79 mmol) of 3,3-[ethylenedioxy17beta-methoxy-16alpha,17alpha-methylene-5alpha,10alpha-oxido-estr-9(11)-ene, which is dissolved in 10 ml of tetrahydrofuran, is instilled cold. Then, it is stirred for 1 hour with the exclusion of moisture, and the solution is heated to room temperature. Then, it is mixed with an aqueous ammonium chloride solution and the steroid is extracted with ether. After the concentration of the extracts by evaporation, the remaining residue is chromatographed on basic aluminum oxide with benzene/ethyl acetate (10:1). 0.65 g of the target compound was isolated in the form of an oil.

IR[cm$^{-1}$]: 1600 (aromatic), 3500 (OH, associated).

j)
11beta-(4-formylphenyl)-17beta-methoxy-16alpha,17alpha-methylene-estra-4,9-dien-3-one 0.6 g of 11beta-(4-(diethoxymethyl)-phenyl)-3,3-ethylenedioxy-17beta-methoxy-16alpha,17alpha-methylene-estr-9-en-5alpha-ol is dissolved in 10 ml of 70% aqueous acetic acid and heated on the water bath for about 2 hours at 70° C. Then, the steroid is precipitated by adding water and some ammonia. The isolated crude product is flash chromatographed with benzene/ethyl acetate (10:1) on neutral aluminum oxide. 0.41 g of the target compound, which can be crystallized from ether or acetonitrile, is obtained, melting point: 196° C. to 199.5° C., $[\alpha]_D=315.9°$.

EXAMPLE 4

The production of reaction steps a to h takes place analogously to example 1.

i)
3,3-ethylenedioxy-11beta-(4-formylphenyl)-17beta-methoxy-16alpha,17alpha-methylene-estr-9-en-5alpha-ol During a test, to finely purify the above-named Grignard product (example 3i) on silica gel (preparative slab, mobile solvent benzene/ethyl acetate 5:1), the diethyl acetate is cleaved and the 11beta-(4-formylphenyl)-3-ketal, which can be crystallized from acetone or methanol, results, melting point: 184° C. to 187° C., $[\alpha]_D=-198.6°$.

EXAMPLE 5 a) 17,17-diethoxy-3-methoxy-estra-1,3,5(10)-triene 5 g of 3-methoxy-estra-1,3,5(10)-trien-17-one is dissolved in 15 ml of absolute ethanol, 15 ml of benzene and 6 ml of formic acid triethyl ester and stirred for 2.5 hours at 50° C. after adding 0.35 g of p-toluenesulfonic acid. After the reaction has been completed, the reaction mixture is used either directly in the next step or is stirred in an aqueous sodium bicarbonate solution, and the steroid is extracted with benzene. The extracts are evaporated to dryness and crystallized from ethanol, and 4.8 g of diethyl ketal is obtained, melting point: 93° C. to 97° C.

b) 17beta-ethoxy-3-methoxy-estra-1,3,5(10),16-tetraene 5 g of 17,17-diethoxy-3-methoxy-estra-1,3,5(10)-triene is dissolved in 20 ml of mesitylene and after addition of 0.3 g of KHSO$_4$ under inert gas is heated within 30 minutes to 40 minutes to 140° C. to 160° C. and is gradually distilled off from the solvent. Then, it is heated for 2 more hours in a vacuum at this temperature and the remaining solvent is distilled off. The remaining residue is used in the next step in the form of an oil without purification. IR[cm$^{-1}$]: 1500, 1575, 1620 (aromatic); 1620 (enol ether superimposed).

c)
17beta-ethoxy-3-methoxy-16alpha,17alpha-methylene-estra-1,3,5(10)-triene 2.5 g of 17beta-ethoxy-3-methoxy-estra-1,3,5(10),16-tetraene is dissolved in 5 ml of benzene and 5 ml of dimethoxyethane and mixed with 5 g of Zn/Cu catalyst (Le Goff) under inert gas. A solution consisting of 4.5 ml of methylene iodide and 4 ml of benzene is instilled in this reaction mixture by gradual gentle heating and vigorous stirring, so that the reaction temperature does not exceed 50° C. After quieting down of the exothermal reaction, the heat bath optionally must be removed in the case of the addition, it is stirred for 4 hours at 50° C. and then filtered from the catalyst. The filtrate is mixed with an aqueous ammonium chloride solution and the steroid is extracted with benzene. The residue remaining after the concentration of the benzene extracts by evaporation is flash chromatographed on neutral aluminum oxide with benzene/n-hexane (1:1). 1.7 g (65% of theory) of the 16alpha-17alpha-methylene compound is obtained, which can be recrystallized from methanol, melting point: 89° C. to 91.5° C., $[\alpha]_D=84°$.

d)

17beta-ethoxy-3-methoxy-16alpha,17-alpha-methylene-estra-2,5(10)-diene

The production took place according to example 1d. The semicrystalline crude product was used directly in the next step.

e)

17beta-ethoxy-16alpha,17alpha-methylene-estr-5(10)-en-3-one

The production took place according to example 1e. Melting point methanol: 94° C. to 96° C., $[\alpha]_D = 174°$.

f)

17beta-ethoxy-16alpha,17alpha-methylene-estra-4,9-dien-3-one

The production took place according to example 1f. Melting point ether/hexane: 104.5° C. to 106.5°, $[\alpha]_D = -160°$.

g)

17beta-ethoxy-3,3-ethylenedioxy-16alpha,17alpha-methylene-estra-5(10),9(11)-diene The production took place according to example 1g. Melting point hexane: 117.5° C. to 118° C., $[\alpha]_D = 207°$.

h)

17beta-ethoxy-3,3-ethylenedioxy-16alpha,17alpha-methylene-5alpha,10alpha-oxido-estr-9(11)-ene 6 g of 17beta-ethoxy-3,3-ethylenedioxy-16alpha,17alpha-methylene-estra-5(10)-9(11)-diene, 2 g of anhydrous Na$_2$HPO$_4$ and 1 g of Na$_2$CO$_3$ are suspended in 30 ml of methylene chloride and, with stirring at room temperature, are mixed with 3.5 ml of 30% H$_2$O$_2$ and finally with 1 g of chloral hydrate. Then, it is stirred for 20 hours at room temperature, then mixed with an aqueous sodium carbonate solution, and the steroid is extracted with methylene chloride. The organic phase is washed twice more with a sodium carbonate solution and finally with water, then dried and concentrated by evaporation. 6.074 g of a slowly crystallizing crude product is obtained which can be recrystallized from hexane.

Melting point: 160° C. to 170° C.

i)

17beta-ethoxy-3,3-ethylenedioxy-11beta-(4-methoxyphenyl)-16alpha,17alpha-methylene-estr-9-en-5alpha-ol 20 ml is taken from a 4-methoxyphenyl magnesium bromide solution prepared by a reaction of 0.48 g of magnesium chips and 2.36 ml of 4-bromoanisole in 20 ml of tetrahydrofuran at 35° C. and mixed with 0.1 g of CuCl under argon and with cooling to $-5°$ C. to $-15°$ C. It is stirred for 15 minutes while maintaining the cooling and then a solution of 1 g of 17beta-ethoxy-3,3-ethylenedioxy-16alpha,17alpha-methylene-5alpha,10alpha-oxido-estr-9(11)-ene in 3 ml of tetrahydrofuran is instilled. Then, it is stirred for 30 minutes at room temperature, then an aqueous ammonium chloride solution is added and the steroid is extracted with methylene chloride. After the concentration of the extracts by evaporation, the residue is flash chromatographed with benzene/ethyl acetate (20:1) on basic aluminum oxide (Greiz-Doelau). After recrystallization, 0.37 g (27% of theory) of the 11beta-anisyl compound is obtained from methanol.

Melting point: 144° C. to 147° C., $[\alpha]_D = 180.4°$.

j)

17beta-ethoxy-11beta-(4-methoxyphenyl)-16alpha,17alpha-methylene-estra-4,9-dien-3-one 0.5 g of 17beta-ethoxy-3,3-ethylenedioxy-11beta-(4-methoxyphenyl)-estr-9-en-5alpha-ol is dissolved in 7 ml of 70% aqueous acetic acid and heated for about 2 hours at a 60° C. water bath temperature. After the reaction has been completed, the steroid is precipitated by addition of water and after separation is flash chromatographed on neutral aluminum oxide with benzene/ethyl acetate (10:1). 0.2 g of 11beta-anisyl-4,9-diene is obtained, which can be crystallized from methanol.

Melting point: 73.5° C. to 74.5° C., $[\alpha]_D = 210.7$.

EXAMPLE 6

The production of reaction steps a to h takes place analogously to example 5.

i)

11beta-(4-dimethylaminophenyl)-17beta-ethoxy-3,3-ethylenedioxy-16alpha,17alpha-methylene-estr-9-en-5alpha-ol 0.05 ml of methyl iodide is added to a suspension of 0.48 g of magnesium chips in 10 ml of tetrahydrofuran and mixed under argon gradually with a solution of 4.2 g of p-bromodimethylaminobenzene in 30 ml of tetrahydrofuran, and the inner temperature should not exceed 50° C. 24 ml is taken from the p-dimethylaminophenyl magnesium bromide solution thus produced and mixed with 0.15 g of CuCl with cooling ($-15°$ C.). It is mixed for about 15 minutes while maintaining this temperature and a solution of 0.75 g of an epoxide enriched with 17beta-ethoxy-3,3-ethylenedioxy-16alpha,17alpha-methylene-5alpha,10alpha-oxido-estr-9(11)-ene in 4 ml of tetrahydrofuran is instilled. Then, it is stirred for 4 hours at a temperature of about 0° C., then an aqueous ammonium chloride solution is added, and the steroid is extracted with methylene chloride. After the concentration of the extracts by evaporation, the residue is flash chromatographed on basic aluminum oxide (Greiz-Doelau). Benzene/ethyl acetate (10:1) serves as a mobile phase. 0.3 g of 11beta-dimethylaminophenyl compound, which can be recrystallized from methanol, is obtained.

Melting point: 117° C. to 119° C., $[\alpha]_D = 31.8°$.

j)

11beta-(4-dimethylaminophenyl)-17beta-ethoxy-16alpha,17alpha-methylene-estra-4,9-dien-3-one The production takes place according to example 1, step j.

Melting point: 84° C. to 87° C., $[\alpha]_D = 355.7°$.

EXAMPLE 7

The production of reaction steps a to h takes place analogously to example 5.

i)

17beta-ethoxy-3,3-ethylenedioxy-16alpha,17alpha-methylene-11beta-[4-(2'-methyl-1',3'-dioxolan-2'-yl)phenyl]-estr-9-en-5alpha-ol 0.05 ml of methyl iodide is added to a suspension of 0.48 g of magnesium chips in 13 ml of THF and mixed gradually under argon with a solution of 4.9 g of 4-bromo-(2'-methyl-1,3-dioxolan-2'-yl-)benzene in 27 ml of THF, and the inner temperature should not exceed 45° C. After dissolution of the magnesium, 40 ml of 4-(2'-methyl-1',3'-dioxolan-2'-yl-)phenyl magnesium bromide is taken and 0.2 g of CuCl is added to it with cooling (−5° C. to −15° C.). It is stirred for 15 minutes while maintaining this temperature and then a solution of 1.69 g of 17beta-ethoxy-3,3-ethylenedioxy-16alpha,1-7alpha-methylene-5alpha,10alpha-oxido-estr-9(11)-ene) in 5 ml of THF is instilled. Then, it is stirred for 1 hour, and the reaction solution is gradually brought to room temperature. After the reaction has been completed, an aqueous ammonium chloride solution is added and the steroid is extracted with methylene chloride. After the concentration of the extracts by evaporation, the remaining residue is chromatographed on basic aluminum oxide (Greiz-Doelau). A benzene/ethyl acetate mixture (20:1) is used as mobile phase. 1.7 g of the 11beta-acetophenylketal compound is obtained, which can be recrystallized from methanol.

Melting point: 95° C. to 97° C., $[\alpha]_D=22.5°$.

11beta-(4-acetylphenyl)-17beta-ethoxy-16alpha,17alpha-methylene-estra-4,9-dien-3-one The production takes place according to example 2, step j.

Melting point methanol/water: 86° C. to 90° C., $[\alpha]_D=280°$.

EXAMPLE 8

The production of reaction steps a to h takes place analogously to example 5.

i)
11beta-[4-(diethoxymethyl)-phenyl]-17beta-ethoxy-3,3-ethylenedioxy-16alpha,17alpha-methylene-estr-9-en-5alpha-ol 1 g (2.69 mmol) of 17beta-ethoxy-3,3-ethylenedioxy-16alpha,17alpha-methylene-5alpha,10alpha-oxido-estr-9(11)-ene is reacted analogously to example 3, step i. After working up and chromatographic purification, which also took place in the way already described, 0.9 g of the Grignard product is isolated in the form of an oil.

IR[cm$^{-1}$]: 1600 (aromatic), 3500 (OH-associated)

j)
17beta-ethoxy-11beta-(4-formylphenyl)-16alpha,17alpha-methylene-estra-4,9-dien-3-one The production takes place according to example 3, step j.

Melting point: 79° C. to 84° C., $[\alpha]_D=411.1°$

EXAMPLE 9

The production of reaction stages a to h takes place analogously to example 5.

i)
17beta-ethoxy-3,3-ethylenedioxy-16alpha,17alpha-methylene-11beta-vinyl-estr-9-en-5alpha-ol 10 ml of a 0.5 m solution of vinylmagnesium bromide in tetrahydrofuran is cooled down to −30° C. and mixed with 0.1 g of CuCl under inert gas. It is stirred for about 15 minutes at this temperature and then 5 ml of a tetrahydrofuran solution containing 0.3 g of 17beta-ethoxy-3,3-ethylenedioxy-16alpha,17alpha-methylene-5alpha,10alpha-oxido-estr-9-ene is instilled cold. Then, it is stirred for 8 hours at a maximum of −15° C. After the completed reaction, it is mixed with aqueous ammonium chloride solution and the steroid is extracted with ether. After chromatography on basic aluminum oxide, a benzene/ethyl acetate mixture (10:1) is used as an eluant, 0.25 g of the 11beta-vinyl compound is isolated in the form of an oil, which is used directly in the next step.

IR[cm$^{-1}$]: 1625 (vinyl), 3500 (OH-associated)

j)
17beta-ethoxy-16alpha,17alpha-methylene-11beta-vinyl-estra-4,9-dien-3-one

The production takes place according to example 1, step j.

$^1$H-NMR[ppm]: 5.61 (1H, 4-ene), 4.95 and 4.77 (3H, vinyl) 1.14; 1.07; 1.00 (Mev O C$_2$H$_5$); 1.03 (3H, 13-Me), 0.6 (2H, cyclopropane)

IR[cm$^{-1}$]: 1600 and 1600 (dienone)

EXAMPLE 10

The production of reaction steps a to h takes place analogously to example 5 and steps i and j analogously to example 1.

k)
11beta-(4-dimethylaminophenyl)-17beta-ethoxy-3,3-ethylenedithio-16alpha,17alpha-methylene-estra-4,9-diene 0.065 g of 11beta-(4-dimethylaminophenyl)-17beta-ethoxy-16alpha,17alpha-methylene-estra-4,9-dien-3-one is dissolved in 0.03 ml of methanol and stirred for 2.5 hours at room temperature after addition of 0.03 ml of thioglycol and 0.03 ml of boron trifluoride etherate. Then, it is mixed with water and the steroid is extracted with ether. After precipitation from methanol/water-/ammonia, 0.063 g of amorphous thioketal is isolated.

Melting point: 109° C. to 114° C., $[\alpha]_D=262.6°$.

EXAMPLE 11 a) 17,17-di-n-butyloxy-3-methoxy-estra-1,3,5(10)-triene 5 g of 3-methoxy-estra-1,3,5(10)-trien-17-one is reacted according to example 1a. N-butanol is used as alcohol. After the reaction has been completed, the reaction mixture is used directly in the next step without intermediate working up.

b) 17-n-butyloxy-3-methoxy-estra-1,3,510),16-tetraene

The reaction mixture obtained in the synthesis of di-n-butyloxy-3-methoxy-estra-1,3,5(10)-triene is mixed with 3 ml of triethylamine and heated to 140° C. to 160° C. under inert gas within 30-40 minutes, and the solvent is distilled off gradually. Finally, it is heated at this temperature for 2 more hours in a vacuum and the remaining solvent is removed. The remaining residue is mixed with sodium bicarbonate solution after cooling and the steroid is extracted with benzene. After chromatography on basic aluminum oxide, benzene/hexane is used as an eluant, 3.95 (66% of theory) of tetraene is obtained, which is further processed in the form of an oil.

IR[cm$^{-1}$]: 1575 and 1620 (aromatic), 1620 (enol ether superimposed)

c)
17beta-n-butyloxy-3-methoxy-16alpha,17alpha-methylene-estra-1,3,5(10)-triene

The production takes place according to example 1c.
Melting point ethanol: 71° C. to 72° C., $[\alpha]_D=80.1°$.

d)
17beta-butyloxy-3-methoxy-16alpha,17alpha-methylene-estra-2,5(10)-diene

The production takes place according to example 1d.
IR[cm$^{-1}$]: 1680 and 1700 (enol ether).

e)
17beta-butyloxy-16alpha,17alpha-methylene-est-5(10)-en-3-one

The production takes place according to example 1e.
IR[cm$^{-1}$]: 1705 (3-ketone).

f)
17beta-butyloxy-16alpha,17alpha-methylene-estra-4,9-dien-3-one

The production takes place according to example 1f.
IR[cm$^{-1}$]: 1600 and 1655 (dienone).

g)
17beta-n-butyloxy-3,3-ethylenedioxy-16alpha,17alpha-methylene-estra-5(10),9(11)-diene The production takes place according to example 1g.
IR[cm$^{-1}$]: no carbonyl.

h)
17beta-butyloxy-3,3-ethylenedioxy-16alpha,17alpha-methylene-5alpha,10alpha-oxido-estr-9(11)-ene The production takes place according to example 1h
IR[cm$^{-1}$]: no carbonyl.

i)
17beta-n-butyloxy-11beta-(4-dimethylaminophenyl)-3,3-ethylenedioxy-estr-9-en-5alpha-ol The production takes place according to example 1i.
Melting point methanol: 147° C. to 151° C., [α]$_D$=22.3°.

j)
17beta-n-butyloxy-11beta-(4-dimethylaminophenyl)-16alpha,17alpha-methylene-estra-4,9-dien-3-one The production takes place according to example 1j.
Melting point methanol/water: 63° C. to 68° C., [α]$_D$=283.6°.

EXAMPLE 12

The production of reaction steps a to h takes place analogously to example 11.

i)
17beta-butyloxy-3,3-ethylenedioxy-16alpha,17alpha-methylene-11beta-[4-(2'-methyl-1',3'-dioxolan-2'-yl)-phenyl]estr-9-en-5alpha-ol The production takes place according to example 2i.
Melting point: 77° C. to 80° C., [α]$_D$=15°.

j)
11beta-(4-acetylphenyl)-17beta-n-butyloxy-16alpha,17alpha-methylene-estra-4,9-dien-3-one 0.39 g of 17beta-butyloxy-3,3-ethylenedioxy-16alpha,17alpha-methylene-11beta-[4-(2'methyl-1',3'-dioxolan-2'-yl)-phenyl]estr-9-en-5alpha-ol is dissolved in 10 ml of 70% aqueous acetic acid and stirred on the water bath at 60° C. for about 1 hour. After the reaction has been completed, the solution is mixed cold with water, and the steroid is precipitated in amorphous crystalline form and can be fritted. After chromatography on basic aluminum oxide with benzene/ethyl acetate (20:1 to 9:1), about 0.25 g of 4,9-dien-3-one, in addition to small amounts of a nonpolar product (11beta-(4-acetylphenyl)-17beta-butyloxy-16alpha,17alpha-methylene-estra-5(10),9(11)-dien-3-one), after precipitation by methanol/water is obtained in the form of an amorphous powder.

Melting point: 63° C. to 67° C., [α]$_D$=171.8°.

EXAMPLE 13 a) 17,17-di-n-hexyloxy-3-methoxy-estra-1,3,5(10)-triene 5 g of 3-methoxy-estra-1,3,5(10)-trien-17-one is reacted according to example 1a. N-hexanol is used as alcohol. The reaction mixture was used in the next step without a preceding working up.

b) n-hexyloxy-3-methoxy-estra-1,3,5(10),16-tetraene

The production takes place according to example 1b.
IR[cm$^{-1}$]: 1575 and 1620 (aromatic), 1620 (enol ether, superimposed).

c)
17beta-n-hexyloxy-3-methoxy-16alpha,17alpha-methylene-estra-1,3,5(10)-triene

The production takes place according to example 1c.
Melting point: 38° C. to 41° C., [α]$_D$=67.7°.

d)
17beta-n-hexyloxy-3-methoxy-16alpha,17alpha-methylene-estra-2,5(10)-diene

The production takes place according to example 1d.
IR[cm$^{-1}$]: 1655 and 1680 (enol ether).

e)
17beta-n-hexyloxy-16alpha,17alpha-methylene-estr-(5(10)en-3-one

The production takes place according to example 1e.
IR[cm$^{-1}$]: 1705 (C=O).

f)
17beta-n-hexyloxy-16alpha,17alpha-methylene-estra-4,9-dien-3-one

The production takes place according to example 1f.
Melting point methanol: 57° C. to 61° C., [α]$_D$=−163.3°.

g)
3,3-ethylenedioxy-17-n-hexyloxy-16alpha,17alpha-methylene-estra-5(10),9(11)-diene The production takes place according to example 1g.
IR[cm$^{-1}$]: no carbonyl.

h)
3,3-ethylenedioxy-17beta-n-hexyloxy-16alpha,17alpha-methylene-5alpha,10alpha-oxido-estr-9(11)-en The production takes place according to example 1h.
IR[cm$^{-1}$]: no carbonyl.

i)
17beta-n-hexyloxy-3,3-ethylenedioxy-16alpha,17alpha-methylene-11beta-[4-(2'-methyl-1',3'-dioxolan-2'-yl)-phenyl]estr-9-en-5alpha-ol The production takes place according to example 2i.
IR[cm$^{-1}$]: 1500 and 1605 (aromatic), 3500 (OH-associated).

j)

11beta-(4-acetylphenyl)-17beta-n-hexyloxy-16alpha,17alpha-methylene-estra-4,9-dien-3-one The production takes place according to example 2j. Melting point methanol: 53° C. to 58° C.

EXAMPLE 14 a)

17,17-di-methoxyethyloxy-3-methoxy-estra-1,3,5(10)triene 5 g of 3-methoxy-estra-1,3,5(10)-trien-17-one is reacted corresponding to example 1a. Ethylene glycol monomethyl ether is used as alcohol. The reaction mixture was used directly in the next step without a preceding working up.

b)

3-methoxy-17beta-methoxyethyloxy-estra-1,3,5(10),16-tetraene

The production takes place according to example 1b.
IR[cm$^{-1}$]: 1575 and 1620 (aromatic), 1620 (enol ether superimposed).

c)

3-methoxy-17beta-methoxyethyloxy-16alpha,17alpha-methylene-estra-1,3,5(10)-triene The production takes place according to example 1c.
Melting point: 86.5° C. to 89° C., [α]$_D$=78.6°.

d)

3-methoxy-17beta-methoxyethyloxy-16alpha,17alpha-methylene-estra-2,5(10)-diene

The production takes place according to example 1d.
Melting point hexane: 80° C. to 96° C., [α]$_D$=116.6°.

e)

17beta-methoxyethyloxy-16alpha,17alpha-methylene-estr-5(10)-en-3-one

The production takes place according to example 1e.
IR[cm$^{-1}$]: 1705 (C=O).

f)

17beta-methoxyethyloxy-16alpha,17alpha-methylene-estra-4,9-dien-3-one

The production takes place according to example 1f.
Melting point hexane: 88.5° C. to 90.5° C., [α]$_D$=−160.2°.

g)

1,3-ethylenedioxy-17beta-methoxyethyloxy-16alpha,17alpha-methylene-estra-5(10),9(11)-diene The production takes place according to example 1g.
IR[cm$^{-1}$]: no C=O.

h)

3,3-ethylenedioxy-17beta-methoxyethyloxy-16alpha,17alpha-methylene-5alpha,10alpha-oxido-estr-9(11)-ene The production takes place according to example 1h.
IR[cm$^{-1}$]: no C=O.

i)

3,3-ethylenedioxy-17beta-methoxyethyloxy-16alpha,17alpha-methylene-11beta-[4-(2'-methyl-1',3'-dioxolan-2'-yl)-phenyl]-estr-9-en-5alpha-ol The production takes place according to example 2i.

IR[cm$^{-1}$]: 1475 and 1595 (aromatic), 3480 (OH-associated).

j)

11beta-(4-acetylphenyl)-17beta-methoxyethyloxy-16alpha,17alpha-methylene-estra-4,9-dien-3-one The production takes place according to example 2j.
Melting point methanol/water: 70° C. to 73.5° C., [α]$_D$=248.3°.

EXAMPLE 15 a)

17-(dimethyl-tert-butyl-silyloxy)-3-methoxy-estra-1,3,5(10),16-tetraene 1.5 g of 3-methoxy-estra-1,3,5(10)-trien-17-one (5.27 mmol) is dissolved with the exclusion of moisture under inert gas in 5 ml of methylene chloride distilled on P$_2$O$_5$ and reacted with 2.4 g of trifluoromethanesulfonic acid-dimethyl-tert-butylsilyl ester and 1.5 ml of triethylamine (KOH dried). Then, it is allowed to stand for 12 hours at room temperature and after the reaction has been completed, the solvent is distilled off in a vacuum. The remaining residue is chromatographed on basic aluminum oxide. Petroleum ether is used as a mobile phase. 2.07 g (98% of theory) of silyl enol ether, which can be crystallized from n-hexane, is obtained.
Melting point: 123° C. to 124.5° C.

b)

17beta-(dimethyl-tert-butylsilyoxy)-3-methoxy-16alpha,17alpha-methylene-estra-1,3,5(10)-triene 1.6 g of 17-(dimethyl-tert-butylsilyloxy)-3-methoxy-estra-1,3,5(10)-16-tetraene is added with exclusion of moisture with stirring to a suspension of 10 g of Zn/Cn catalyst in 15 ml of dimethoxyethane and 15 ml of diethyl ether and 7 ml of methylene iodide is instilled in it within 10 minutes. Then, it is stirred for 20 hours at 50° C. Then, the reaction mixture with cooling is carefully mixed with a solvent mixture consisting of 6 ml of pyridine, 10 ml of diethyl ether and 6 ml of pentane, and the entire mixture is filtered on basic or neutral aluminum oxide and exhaustively rewashed with ether/pentane. The combined filtrates are evaporated to dryness and the remaining residue is flash chromatographed on basic aluminum oxide. A benzene/pentane mixture (1:1) is used as mobile phase. After recrystallization, 0.64 g of the cyclopropane product is obtained from hexane or ethanol.
Melting point (from ethanol): 106° C. to 107° C.

c)

17beta-(dimethyl-tert-butylsilyloxy)-3-methoxy-16alpha,17alpha-methylene-estra-2,5(10)-diene 5 ml of a tetrahydrofuran solution containing 0.42 g of 17beta-(dimethyl-tert-butylsilyloxy)-3-methoxy-16alpha,17alpha-methylene-estra-1,3,5(10)-triene is slowly instilled in a freshly-prepared Birch solution, consisting of 40 ml of tetrahydrofuran, 200 ml of ammonia, 8 ml of tert-butanol and 0.25 g of lithium at about −35° C. After a 1.5 hour stirring with reflux, the still blue solution is bleached by addition of ammonium chloride (excess), then the ammonia is evaporated off, the remaining suspension is filtered on neutral aluminum oxide, washed thoroughly with ether and the combined filtrates are evaporated to dryness in a vacuum. 0.42 g of a colorless oil is obtained as a thin-layer chromatographically homogeneous product, which is used in this form in the next step.

IR[cm$^{-1}$]: 1690 and 1655 (dienol ether)

d)
17beta-(dimethyl-tert-butylsilyloxy)-16alpha,17alpha-methylene-estr-5(10)-en-3-one 0.42 g of 17beta-(dimethyl-tert-butylsilyloxy)-16alpha,17alpha-methylene-estra-2,5(10)-diene is suspended in 12 ml of 80% aqueous acetone and mixed with 0.012 ml of 25% sulfuric acid. It is stirred for 2 hours at room temperature and then ice water is slowly added, and the steroid is precipitated. The steroid is suctioned off, washed with bicarbonate solution and finally washed neutral with water. 0.3 g of the amorphous crystalline 3-keto-5(10)-product, which is used in this form in the next step, is obtained. IR[cm$^{-1}$]: 1707 (C=O)

e)
17beta-(dimethyl-tert-butylsilyloxy)-16alpha,17alpha-methylene-estr-4,9-dien-3-one 0.35 g of 17beta-(dimethyl-tert-butylsilyloxy)-16alpha,17alpha-methylene-estr-5(10)-en-3-one is dissolved in 10 ml of pyridine (KOH dried) and mixed with 0.45 g of pyridine hydrobromide perbromide at −30° C. under inert gas. Then, it is stirred for 20 minutes at −5° C., then, the excess bromation agent is destroyed by adding 2-methylbut-2-ene. Then, it is stirred for 4 hours at room temperature. After the reaction has been completed, it is stirred in ice water and the steroid is extracted with ether. The residue remaining after the concentration by evaporation is chromatographed on basic aluminum oxide with benzene/ethyl acetate (10:1). 0.2 g of 4,9-dien-3-one-silyl ether is obtained, which can be crystallized from aqueous methanol.

Melting point: 114.5° C. to 115.5° C., [α]$_D$=−138.8°.

f)
17beta-(dimethyl-tert-butylsilyloxy)-3,3-ethylenedioxy-16alpha,17alpha-methylene-estra-5(10),9(11)-diene 4.3 g of 17beta-(dimethyl-tert-butylsilyloxy)-16alpha,17alpha-methylene-estra-4,9-dien-3-one is dissolved in 100 ml of benzene, mixed with 5 ml of glycol and 0.2 g of p-toluenesulfonic acid and boiled for 1 hour on the water separator. Then, it is stirred in a saturated sodium bicarbonate solution and the steroid is extracted with benzene. After concentration of the extracts by evaporation, the remaining thinlayer-chromatographically homogeneous oily residue is crystallized from aqueous methanol.

Melting point: 68.5° C. to 70° C.

g)
17beta-(dimethyl-tert-butylsilyloxy)-3,3-ethylenedioxy-5alpha,10alpha-epoxy-16alpha,17alpha-methylene-estr-9(11)-ene 1 g of 17beta-(dimethyl-tert-butylsilyloxy)-3,3-ethylenedioxy-16alpha,17alpha-methylene-estra-5(10),9(11)-diene is dissolved in 22.5 ml of acetonitrile and 10 ml of methylene chloride and mixed with 0.722 g of m-chloroperbenzoic acid with ice cooling. It is stirred for 15 minutes while maintaining the cooling, then a saturated aqueous sodium carbonate solution is added and the steroid is extracted with methylene chloride, after previously adding 3 drops of triethylamine with the methylene chloride. After concentration of the extracts by evaporation, it is flash chromatographed on basic aluminum oxide. Benzene is used as mobile phase. 0.8 g of 5alpha,10alpha-epoxide in obtained in the form of an oil, which is used in this form in the next step.

IR[cm$^{-1}$]: no C=O, no OH h)
11beta-(4-dimethylaminophenyl)-17beta-(dimethyl-tert-butylislyloxy)-3,3-ethylenedioxy-16alpha,17alpha-methylene-estr-9-en-5alpha-ol 0.05 ml of 1,2-dibromoethane is added to a suspension of 0.48 g of magnesium chips in 10 ml of tetrahydrofuran, and mixed under argon gradually with a solution of 4.2 g of p-bromodimethylaminobenzene in 30 ml of tetrahydrofuran, and the inner temperature should not exceed 50° C. 30 ml is taken from the p-dimethylaminophenylmagnesium bromide solution thus produced is taken and mixed with 0.18 g of CuCl with cooling (−15° C.). It is stirred for about 15 minutes while maintaining this temperature and then a solution of 1.8 g of 17beta-(dimethyl-tert-butylsilyloxy)-3,3-ethylenedioxy-16alpha,17alpha-methylene-5alpha,10alpha-epoxy-estra-9(11)-ene in 6 ml of tetrahydrofuran is instilled. Then, it is stirred for 2.5 hours at a temperature of about 0° C., then an aqueous ammonium chloride solution is added and the steroid is extracted with methylene chloride. After the concentration of the extracts by evaporation, the residue is flash chromatographed on basic aluminum oxide (Greiz-Doelau). Benzene/ethyl acetate (40:1) is used as mobile phase. 1.7 g of the concentrated 11beta-dimethylamino compound is obtained, which can be directly further processed as oil.

IR[cm$^{-1}$]: 3500 (OH, associated), 1610 and 1500 (aromatic).

i)
11beta-(4-dimethylaminophenyl)-17beta-(dimethyl-tert-butylsilyloxy)-16alpha,17alpha-methylene-estra-4,9-dien-3-one 0.4 g of 11beta-(4-dimethylaminophenyl)-17beta-(dimethyltert-butylsilyloxy)-3,3-ethylenedioxy-16alpha,17alpha-methylene-estr-9-en-5alpha-ol is dissolved in 10 ml of 70% aqueous acetic acid and stirred for 2 hours on the water bath at 60° C. After the reaction has been completed, the steroid is precipitated by addition of water and some dilute ammonia solution. The crude product thus obtained is purified by chromatography on neutral aluminum oxide (Greiz-Doelau) with benzene/ethyl acetate (20:1). 0.31 g of the 11beta-dimethylamino compound, which can be crystallized from methanol/water, is obtained.

Melting point: 100° C. to 102.5° C., [α]$_D$=222.3°.

EXAMPLE 16 a)
3-methoxy-17-trimethylsilyloxy-estra-1,3,5(10),16-tetraene 20.3 g (72 mmol) of 3-methoxy-estra-1,3,5(10)-trien-17-one is suspended with exclusion of moisture in 80 ml of acetonitrile (P$_2$O$_5$ and molecular sieve dried) and mixed with 17.4 ml of triethylamine (125 mmol, dried on KOH) as well as with 12.24 ml of trimethylchlorosilane (96 mmol) at an inner temperature of 35° C. Then, an NaI solution, which contains 15 g of NaI (96 mmol) in 100 ml of acetonitrile (NaI dried at 140° C. in a vacuum), is instilled in this suspension, so that the reaction temperature is kept at 35° C. without external heating. The reaction performed under nitrogen is performed with vigorous stirring. It is seen that after the addition has been completed, the amount of undissolved initial product becomes smaller. Later, the crystals completely disappeared. After 1.5 hours, the silyl enol ether begins to crystallize. After 4 hours, the crystal suspension is stirred in ice water, to which some triethylamine was added. Then, it is fritted, rewashed with water, sucked dry and the substance dried on $P_2O_5$ in a vacuum. 25.4 g of silyl enol ether, which can be recrystallized from hexane or methanol, is obtained.

Melting point: 80° C. to 84° C.

b)
3-methoxy-16alpha,17alpha-methylene-17beta-trimethylsilyloxy-estra-1,3,5(10)-triene 10 g of 3-methoxy-17-trimethylsilyloxy-estra-1,3,5(10),16-tetraene is dissolved in 20 ml of benzene and 20 ml of dimethoxyethane and mixed under inert gas with 20 g of Zn/Cu catalyst (Le Goff). 15 ml of methylene iodide is gradually added to this reaction mixture with gentle heating and vigorous stirring, so that a reaction temperature of approximately 50° C. is maintained. Then, it is stirred at 50° C. for 4 hours. After the reaction has been completed, it is filtered off from the catalyst, the filtrate is mixed with an aqueous ammonium chloride solution and the steroid is extracted with benzene. The residue remaining after the concentration of the extracts by evaporation, is flash chromatographed on basic aluminum oxide with a benzene/n-hexane mixture (1:11). 4.4 g (53% of theory) of the 16alpha-17alpha-methylene compound, which can be crystallized from n-hexane, is obtained.

Melting point: 118° C. to 119° C.

c)
3-methoxy-16alpha,17alpha-methylene-17-beta-trimethylsilyloxy-estra-2,5-(10)-diene 50 ml of a tetrahydrofuran solution containing 10 g of 3-methoxy-16alpha,17alpha-methylene-17beta-trimethylsilyloxy-estra-1,3,5(10)-triene is slowly instilled in a freshly-prepared homogeneous Birch solution consisting of 250 ml of tetrahydrofuran, 650 ml of liquid ammonia, 30 ml of tert-butanol and 1.9 g of lithium at about −35° C. After a 4-hour stirring, the still blue solution is bleached by addition of ammonium chloride (excess), then the ammonia is evaporated off, the remaining suspension is filtered on neutral aluminum oxide, washed thoroughly with ether, and the combined filtrates are evaporated to dryness in a vacuum. 10.3 g of a colorless oil, which can be crystallized from n-hexane, is obtained.

Melting point: 107.5° C. to 112.5° d)
17beta-hydroxy-16alpha,17alpha-methylene-estr-5(10)-en-3-one 3.32 g of 3-methoxy-16alpha,17alpha-methylene-17beta-trimethylsilyloxy-estra-2,5(10)-diene is dissolved in 40 ml of 80% aqueous acetone and mixed with 0.16 ml of 20% sulfuric acid. It is stirred for 2 hours at room temperature and then ice water is added slowly, and the steroid is precipitated. The steroid is suctioned off, washed with bicarbonate solution and finally neutral with water. 2.3 g of the 3-keto-5(10) compound, which can be recrystallized from aqueous methanol, is obtained.

Melting point: 141° C. to 147° C.

e)
17beta-acetoxy-16alpha,17alpha-methylene-estra-4,9-dien-3-one

About 5.2 g of dienone obtained in the bromation/-dehydrobromation of 17beta-hydroxy-16alpha,17alpha-methylene-estr-5(10)-en-3-one analogously to 15 e) is acetylated directly in the pyridine solution without working up. In this case, the procedure followed is that the reaction mixture is mixed with 6 ml of acetic anhydride after quietened-down dehydrobromation and stirred for 16 hours at room temperature. After the reaction has been completed, it is stirred in ice water, to which some hydrochloric acid was added, and the steroid is extracted with methylene chloride. The residue remaining after the concentration of the extracts by evaporation is chromatographed on neutral aluminum oxide. A benzene/ethyl acetate mixture (10:1) is used as mobile phase. 3.99 g of the product crystallizing from heptane/benzene is obtained.

Melting point: 137° C. to 138.5° C., $[\alpha]_D = 168.1°$.

f)
17beta-acetoxy-3,3-ethylenedioxy-16alpha,17alpha-methylene-estra-5(10),9(11)-diene 5 g of 17beta-acetoxy-16alpha,17alpha-methylene-estra-4,9-dien-3-one is dissolved in 108 ml of benzene, mixed with 5 ml of glycol and 0.2 g of p-toluenesulfonic acid and boiled for 2 hours on the water separator. Then, it is stirred in an aqueous saturated sodium bicarbonate solution and the steroid is extracted with benzene. After chromatography on basic aluminum oxide and concentration of the eluates by evaporation, the thin-layer-chromatographically homogeneous residue is directly further processed.

IR: no C=O g)
17beta-acetoxy-3,3-ethylenedioxy-5alpha,10alpha-epoxy-16alpha,17alpha-methylene-estr-9(11)-ene 5 g of 17beta-acetoxy-3,3-ethylenedioxy-16alpha,17alpha-methylene-estra-5(10),9(11)-diene, 2 g of anhydrous $Na_2HPO_4$ and 1 g of $Na_2CO_3$ are suspended in 45 ml of methylene chloride and mixed with 7.25 ml of 30% $H_2O_2$ with stirring at room temperature and finally with 1.25 g of chloral hydrate. Then, it is stirred for 20 hours at room temperature and following this, an aqueous sodium carbonate solution is added and the steroid is extracted with methylene chloride. The organic phase is washed twice more with a sodium carbonate solution and finally with water, then dried and concentrated by evaporation. The remaining residue is flash chromatographed on basic aluminum oxide with benzene/ethyl acetate (20:1 to 9:1). 4.25 g of 5alpha,10alpha-epoxide is obtained as an oil, which is used directly in the next step.

h)
11beta-(4-acetylphenyl)-16alpha,17alpha-methylene-estra-4,9-dien-17beta-ol The production of step h takes place analogously to example 15.

i) 17beta-acetoxy-11beta-(4-acetylphenyl)-16alpha,17alpha-methylene-estra-4,9-dien-3-one 0.4 g of 11beta-(4-acetylphenyl)-16alpha,17alpha-methylene-estra-4,9-dien-17beta-ol is dissolved in 2 ml of pyridine and allowed to stand at room temperature for 16 hours after addition of 1 ml of acetic anhydride and 0.005 g of dimethylaminopyridine. Then, it is stirred in ice water and the precipitated product is fritted. For purification, the crude product is flash chromatographed on neutral aluminum oxide with benzene/ethyl acetate (10:1). 0.25 g of 11beta-acetoxy-4,9-dien-3-one, which can be recrystallized from methanol, is obtained.

Melting point: 108° C. to 111° C., $[\alpha]_D = 257.3°$.

EXAMPLE 17

The production of steps a to d takes place analogously to example 16.

e)
17beta-hydroxy-16alpha,17alpha-methylene-estra-4,9-dien-3-one 2.3 g of 17beta-hydroxy-16alpha,17alpha-methylene-estr-5(10)-en-3-one is dissolved in 20 ml of pyridine dried on KOH and is mixed at −30° C. with stirring in an inert gas atmosphere with 2.88 g of pyridine hydrobromide perbromide. Then, it is stirred for about 15 minutes at a temperature of about −5° C. and then the excess bromation agent is destroyed by addition of dihydropyrane. Then, it is stirred for 4 hours at room temperature, the reaction mixture is mixed with water and the steroid is extracted with methylene chloride. After the concentration of the extracts by evaporation, the remaining residue is chromatographed on silica gel. A benzene/ethyl acetate mixture (5:1 to 2:1) is used as mobile phase. 1.6 g of dienone, which can be crystallized from aqueous methanol, is obtained.

Melting point: 191° C. to 193° C., $[\alpha]_D = 139.1°$.

f)
17beta-(dimethyl-tert-butylsilyloxy)-16alpha,17alpha-methylene-estra-4,9-dien-3-one The dienone obtained after the bromation/dehydrobromation of 17beta-hydroxy-16alpha,17alpha-methylene-estr-5(10)-en-3-one analogously to 15 e) is silylated directly in the pyridine solution without working up. In this case, the procedure followed is that after quietened-down dehydrobromation, 2.41 g (16 mmol) of dimethyl-tert-butyl-chlorosilane and 3.4 g (50 mmol) of imidazole are added and stirred for 2 to 2.5 hours at room temperature. Then, it is mixed with ice water and dilute hydrochloric acid and the steroid is extracted with ether. The residue obtained after the concentration by evaporation is chromatographed on basic aluminum oxide with benzene/ethyl acetate (10:1). 2.35 g (68% of theory) of silylether is obtained, which can be crystallized from aqueous methanol.

Melting point: 114.5° C. to 115.5° C., $[\alpha]_D = -138.8°$ h)
17beta-(dimethyl-tert-butylsilyloxy)-3,3-ethylenedioxy-11beta-(4-methoxyphenyl)-16alpha,17alpha-methylene-estr-9-en-5alpha-ol 20 ml is taken from a 4-methoxyphenyl magnesium bromide solution prepared by reaction of 0.48 g of magnesium chips and 2.36 ml of p-bromoanisole in 20 ml of tetrahydrofuran at 35° C. and mixed with 0.1 g of CuCl under argon and with cooling to −5° C. to −15° C. It is stirred for 15 minutes while maintaining the cooling and then a solution of 1 g of 17beta-(dimethyl-tert-butylsilyloxy)-3,3-ethylenedioxy-16alpha,17alpha-methylene-5alpha,10alpha-epoxy-estr-9(11)-ene in 4 ml of tetrahydrofuran is instilled. Then, it is stirred for 30 minutes at room temperature, then an aqueous ammonium chloride solution is added and the steroid is extracted with methylene chloride. After the concentration of the extracts by evaporation, the residue is flash chromatographed on basic aluminum oxide (Greiz-Doelau) with benzene/ethyl acetate (40:1). 0.85 g of the 11beta-anisyl compound is isolated as an oil.

IR[cm$^{-1}$]: 3500 (OH, associated), 1605, 1580 and 1500 (aromatic).

i)
17beta-hydroxy-16alpha,17alpha-methylene-11beta-(4-methoxyphenyl)-estra-4,9-dien-3-one 0.94 g of 17beta-(dimethyl-tert-butylsilyloxy)-3,3-ethylenedioxy-11beta-(4-methoxyphenyl)-16alpha-methylene-estr-9-en-5alpha-ol is dissolved in 10 ml of 70% aqueous acetic acid and stirred for 2 hours on the water bath at 60° C. After the reaction has been completed, the steroid is precipitated by addition of water. The thus obtainable crude product is purified by chromatography on neutral aluminum oxide (Greiz-Doelau), a benzene/ethyl acetate mixture (3:1) is used as mobile phase. 0.23 g of the 11beta-anisyl compound, which can be crystallized from methanol/water, is obtained.

Melting point: 107° C. to 110° C., $[\alpha]_D$: 210.1°.

EXAMPLE 18

The production of steps a to g takes place analogously to example 15.

h)
17beta-(dimethyl-tert-butylsilyloxy)-3,3-ethylenedioxy-16alpha,17alpha-methylene-11beta[4-(2'-methyl-1',3'-dixolan-2'-yl-)phenyl]-estr-9-en-5alpha-ol 0.05 ml of 1.2 dibromoethane is added to a suspension of 0.48 g of magnesium chips in 13 ml of tetrahydrofuran and gradually mixed under argon with a solution of 4.9 g of p-bromo(2'-methyl-1',3'-dioxolan-2'-yl)benzene in 27 ml of tetrahydrofuran, and the inner temperature should not exceed 45° C. After dissolution of the magnesium, 30 ml of 4-(2'-methyl-1',3'-dioxolan-2'-yl)-phenyl-magnesium bromide solution is taken and 0.2 g of CuCl is added with cooling (−5° C. to −15° C.). It is stirred for 15 minutes while maintaining this temperature and then a solution of 1.62 g of 17beta-(dimethyl-tert-butylsilyloxy)-3,3-ethylenedioxy-16alpha,17alpha-methylene-5alpha,10alpha-epoxy-estr-9(11)-ene in 7 ml of tetrahydrofuran is instilled. Then, it is stirred for one hour, and the reaction solution is brought gradually to room temperature. After the reaction has been completed, an aqueous ammonium chloride solution is added and the steroid is extracted with methylene chloride. After concentration of the extracts by evaporation, the remaining residue is flash chromatographed on basic aluminum oxide (Greiz-Doelau) with benzene/ethyl acetate (20:1). 1.6 of the acetophenylketal compound, which can be recrystallized from methanol, is obtained.

Melting point: 144° C. to 152° C. (semicrystalline).

i)
11beta-(4-acetylphenyl)-17beta-hydroxy-16alpha,17alpha-methylene-estra-4,9-dien-3-one 0.4 g of 17beta-(dimethyl-tert-butylsilyloxy)-3,3-ethylenedioxy-16alpha,17alpha-methylene-11beta-[4-(2'-methyl-1',3'-dioxolan-2'-yl)phenyl]-estr-9-en-5alpha-ol is dissolved in 10 ml of 70% aqueous acetic acid and stirred for 2 hours on the water bath at 60° C. After the reaction has been completed, the steroid is precipitated by addition of water. The crude product obtained is purified by chromatography on neutral aluminum oxide (Greiz-Doelau), a benzene/ethyl acetate mixture (5:1) is used as mobile phase. 0.28 g of the 11beta-acetophenyl compound, which can be crystallized from methanol/water, is obtained.

Melting point: 123° C. to 128° C., $[\alpha]_D=268.7°$.

EXAMPLE 19

The production of steps a to e takes place analogously to example 16.

f)
3,3-ethylenedioxy-17beta-methoxymethylene-oxy-16alpha,17alpha-methylene-estra-5(10),9(11)-diene 3.6 g of 17beta-acetoxy-3,3-ethylenedioxy-16alpha,17alpha-methylene-estra-5(10),9(11)-diene is dissolved under argon in 25 ml of absolute tetrahydrofuran and stirred for 3 hours at 50° C. after addition of 0.512 g of naphthalene and 0.2 g of lithium. It is allowed to cool to room temperature, then is mixed with a tetrahydrofuran solution containing 1.5 ml of chloromethyl methyl ether, and is allowed to stand overnight. Then, water is added and the steroid is extracted with ether. The residue obtainable after the concentration by evaporation is chromatographed on basic aluminum oxide. A benzene/ethyl acetate mixture (10:1) is used as mobile phase. 2.5 g of 17beta-methoxymethyl ether is obtained as an oil, which is used directly in the next step.

IR: no C=O.

g)
3,3-ethylenedioxy-17beta-methoxymethylene-oxy-16alpha,17alpha-methylene-5alpha,10alpha-epoxy-estr-9(11)-ene The production takes place analogously to example 15 g).

The compound is isolated as an oil.
IR[cm$^{-1}$]: no C=O.

h)
3,3-ethylenedioxy-17beta-methoxymethylene-oxy-11beta-[4-(2'-methyl-1',3'-dioxolan-2'-yl-)phenyl]-16alpha,17alpha-methylene-estr-9-en-5alpha-ol The production takes place analogously to example 18 h).

Melting point (from methanol): 150° C. to 155° C., $[\alpha]_D$: 44.9°.

i)
11beta-(4-acetylphenyl)-17beta-methoxymethylene-oxy-16alpha,17alpha-methylene-estra-4,9-dien-3-one The production takes place analogously to example 17 i).

Melting point: 70° C. to 74° C., $[\alpha]_D$: 290.1°.

EXAMPLE 20

The production of steps a to h takes place analogously to example 15.

i)
11beta-(4-dimethylaminophenyl)-17beta-hydroxy-16alpha,17alpha-methylene-estra-4,9-dien-3-one 0.5 g of 11beta-(4-dimethylaminophenyl)-17beta-(dimethyltert-butylsilyloxy)-3,3-ethylenedioxy-16alpha,17alpha-methylene-estr-9-en-5alpha-ol is dissolved in 10 ml of 70% aqueous acetic acid and stirred for 10 hours on the water bath at a bath temperature of 70° C.

After the reaction has been completed, the steroid is precipitated by addition of water and some dilute ammonia solution. The crude product is purified by chromatography on neutral aluminum oxide (Greiz/Doelau) with benzene/ethyl acetate (5:1). 0.3 g of the 11beta-dimethylaminophenyl compound, which can be crystallized from methanol/water, is obtained.

Melting point: 137° C. to 140° C., $[\alpha]_D=287.6°$.

EXAMPLE 21

Production of 17-alkoxy-16alpha,17alpha-methylene compounds a)
3-methoxy-17-trimethylsilyloxy-estra-1,3,5(10),16-tetraene 10 g of 3-methoxy-estra-1,3,5(10)-trien-17-one (35.2 mmol) is mixed with exclusion of moisture under inert gas with 30 ml of methylene chloride distilled on $P_2O_5$ and 10.5 g of trifluoromethanesulfonic acid trimethylsilyl ester (47.2 mmol, D=1.15). Then, about 7 ml of triethylamine (KOH dried, M=101.2; D=0.726) is added in portions with stirring and gentle cooling, and the solution reacts clearly in an alkaline way. Then, it is allowed to stand for 12 hours at room temperature, and after the reaction has been completed, the solvent is removed in a vacuum. The remaining viscous residue is extracted three times with about 20 ml of absolute ether under inert gas. The ether solution, in which the steroid is present, is used directly in the next step.

The production of step b takes place analogously to example 16.

b')
17beta-hydroxy-3-methoxy-16alpha,17alpha-methylene-estra-1,3,5(10)-triene 0.2 g of 3-methoxy-16alpha,17alpha-methylene-17beta-trimethylsilyloxy-estra-1,3,5(10)-triene is heated on the water bath together with 5 ml of methanol and 0.05 g of pyridinium tosylate for 30 minutes. After the saponification has been completed, it is mixed with sodium bicarbonate solution and the steroid is extracted with methylene chloride. After the concentration of the extracts by evaporation, it is recrystallized from methanol/water, and 0.13 g of the 17beta-hydroxy compound is obtained.

Melting point: 114° C. to 116° C.

b")
3,17-dimethoxy-16alpha,17alpha-methylene-estra-1,3,5(10)-triene 0.1 g of 17beta-hydroxy-3-methoxy-16alpha,17alpha-methylene-estra-1,3,5(10)-triene is dissolved in 5 ml of absolute tetrahydrofuran and mixed by instillation at room temperature with a 0.5 molar lithium naphthalide solution in tetrahydrofuran, until the solution is no longer bleached. Following this, 0.1 ml of methyl iodide is added and stirred with gentle heating for about 30 minutes. After the reaction has been completed, water is added, and the steroid is extracted with ether. The residue remaining after the concentration of the ether extracts by evaporation is chromatographed on neutral aluminum oxide. The elution takes place with benzene. 0.1 g of 17beta-methyl ether, which can be crystallized from methanol, is obtained.

Melting point: 128° C. to 131.5° C., $[\alpha]_D$: 93.5°.

We claim:

1. An 11β-substituted-16α,17α-methylene-estra 4,9-dien-3-one of formula I

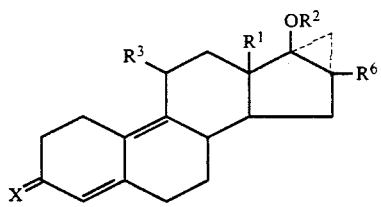

wherein
R¹ is a methyl or ethyl group;
R² is H; a $C_{1-6}$-alkyl, -alkoxymethyl, -alkanoyl or -alkoxycarbonyl group; 2-methoxyethyl; 2-hydroxyethyl; 2-$C_{1-4}$-alkanoyloxyethyl; or a tri-$C_{1-4}$-alkylsilyl group;
R³ is vinyl; a $C_{1-6}$-alkyl; or a phenyl radical para-substituted by —OCH₃, —SCH₃, —N(CH₃)₂, —NHCH₃, —CN, —CHO, —C(O)CH₃, CH₃CHOH— or —CH₂OH;
R⁶ is H or a $C_{1-4}$-alkyl group; and
X is O, a hydroxy- or methoxyimino group (=N~OH or =N~OCH₃), or a cyclic thioketal with 2 or 3 carbon ring atoms.

2. A compound of claim 1, wherein
R¹ is a methyl group,
R² is H; a $C_{1-6}$-alkyl; a tri-$C_{1-4}$-alkylsilyl group; or an acetyl-, —CH₂OCH₃— or 2-methoxyethyl group,
R³ is vinyl or a phenyl radical para-substituted by —N(CH₃)₂, —CHO, —C(O)CH₃, or —OCH₃,
R⁶ is H or a methyl group, and
X is O.

3. A compound of claim 1, namely
-17beta-ethoxy-11beta-(4-methoxyphenyl)-16alpha,17alpha-methylene-estra-4,9-dien-3-one,
-11beta-(4-dimethylaminophenyl)-17beta-methoxy-16alpha,17alpha-methylene-estra-4,9-dien-3-one,
-11beta-(4-dimethylaminophenyl)-17beta-ethoxy-16alpha,17alpha-methylene-estra-4,9-dien-3-one,
-17beta-butyloxy-11beta-(4-dimethylaminophenyl)-16alpha,17alpha-methylene-estra-4,9-dien-3-one,
-11beta-(4-acetylphenyl)-17beta-methoxy-16alpha,17alpha-methylene-estra-4,9-dien-3-one,
-11beta-(4-acetylphenyl)-17beta-ethoxy-16alpha,17alpha-methylene-estra-4,9-dien-3-one,
-11beta-(4-acetylphenyl)-17beta-butyloxy-16alpha,17alpha-methylene-estra-4,9-dien-3-one,
-11beta-(4-acetylphenyl)-17beta-hexyloxy-16alpha,17alpha-methylene-estra-4,9-dien-3-one,
-11beta-(4-acetylphenyl)-17beta-methoxyethyloxy-16alpha,17alpha-methylene-estra-4,9-dien-3-one,
-11beta-(4-formylphenyl)-17beta-methoxy-16alpha,17alpha-methylene-estra-4,9-dien-3-one,
-17beta-ethoxy-11beta-(4-formylphenyl)-16alpha,17alpha-methylene-estra-4,9-dien-3-one,
-17beta-(dimethyl-tert-butylsiloxy)-11beta-(4-methoxyphenyl)-16alpha,17alpha-methylene-estra-4,9-dien-3-one,
-11beta-(4-dimethylaminophenyl)-17beta-(dimethyl-tert-butylsiloxy)-16alpha,17alpha-methylene-estra-4,9-dien-3-one,
-11beta-(4-acetylphenyl)-17beta-(dimethyl-tert-butylsiloxy)-16alpha,17alpha-methylene-estra-4,9-dien-3-one,
-17beta-hydroxy-11beta-(4-methoxyphenyl)-16alpha,17alpha-methylene-estra-4,9-dien-3-one,
-11beta-(4-dimethylaminophenyl)-17beta-hydroxy-16alpha,17alpha-methylene-estra-4,9-dien-3-one,
-11beta-(4-acetylphenyl)-17beta-hydroxy-16alpha,17alpha-methylene-estra-4,9-dien-3-one,
-17beta-acetoxy-11beta-(4-dimethylaminophenyl)-16alpha,17alpha-methylene-estra-4,9-dien-3-one,
-17beta-acetoxy-11beta-(4-acetylphenyl)-16alpha,17alpha-methylene-estra-4,9-dien-3-one,
-11beta-(4-dimethylaminophenyl)-17beta-methoxymethyl-16alpha,17alpha-methylene-estra-4,9-dien-3-one,
-11beta-(4-acetylphenyl)-17beta-methoxymethyl-16alpha,17alpha-methylene-estra-4,9-dien-3-one,
-11beta-(4-dimethylaminophenyl)-17beta-methoxy-16beta-methyl-16alpha,17alpha-methylene-estra-4,9-dien-3-one and
-11beta-(4-acetylphenyl)-17beta-methoxy-16alpha,17alpha-methylene-estra-4,9-dien-3-one.

4. A pharmaceutical preparation comprising a compound of claim 1 and a pharmaceutically acceptable excipient.

5. A method of inducing labor, comprising administering to a pregnant patient an effective amount of a compound of claim 1.

6. A method of inducing abortion, comprising administering to a pregnant patient an effective amount of a compound of claim 1.

7. A method of treating endometriosis, comprising administering to a patient an effective amount of a compound of claim 1.

8. A method of treating dysmenorrhea, comprising administering to a patient an effective amount of a compound of claim 1.

9. A method of treating endocrine hormone-dependent tumors, comprising administering to a patient an effective amount of a compound of claim 1.

10. A method of inducing an antigestagenic effect in a patient, comprising administering an effective amount of a compound of claim 1.

* * * * *